United States Patent
Gosain et al.

(10) Patent No.: US 10,110,568 B2
(45) Date of Patent: Oct. 23, 2018

(54) KEYLESS ACCESS TO LAPTOP

(71) Applicant: Dell Products, LP, Round Rock, TX (US)

(72) Inventors: Rohit Gosain, Bangalore (IN); Daniel L. Hamlin, Round Rock, TX (US)

(73) Assignee: DELL PRODUCTS, LP, Round Rock, TX (US)

( * ) Notice: Subject to any disclaimer, the term of this patent is extended or adjusted under 35 U.S.C. 154(b) by 175 days.

(21) Appl. No.: 15/014,599

(22) Filed: Feb. 3, 2016

(65) Prior Publication Data

US 2017/0222982 A1    Aug. 3, 2017

(51) Int. Cl.
*H04L 29/06* (2006.01)
*H04W 12/06* (2009.01)
*H04W 4/80* (2018.01)

(52) U.S. Cl.
CPC .......... *H04L 63/0428* (2013.01); *H04L 63/08* (2013.01); *H04L 63/0807* (2013.01); *H04W 4/80* (2018.02); *H04W 12/06* (2013.01)

(58) Field of Classification Search
CPC . H04L 63/04; H04L 63/1408; H04L 63/0428; H04L 63/08; H04W 4/02; H04W 48/10
USPC .................. 713/168–169, 170; 726/9, 22
See application file for complete search history.

(56) References Cited

U.S. PATENT DOCUMENTS

| | | | |
|---|---|---|---|
| 7,475,248 B2 | 1/2009 | Barrus et al. | |
| 9,189,900 B1* | 11/2015 | Penilla | G07C 9/00007 |
| 9,674,705 B2* | 6/2017 | Rose | H04W 12/06 |
| 9,894,473 B2* | 2/2018 | Britt | H04L 63/06 |
| 2004/0227615 A1 | 11/2004 | John et al. | |
| 2007/0202806 A1 | 8/2007 | Kim | |
| 2007/0220253 A1* | 9/2007 | Law | G06F 21/445 |
| | | | 713/168 |
| 2013/0138496 A1* | 5/2013 | Jin | G06Q 30/02 |
| | | | 705/14.26 |
| 2015/0381618 A1* | 12/2015 | Lin | H04L 63/0869 |
| | | | 713/169 |

* cited by examiner

Primary Examiner — Jahangir Kabir
(74) Attorney, Agent, or Firm — Larson Newman, LLP (57) ABSTRACT

A method including transmitting, by a mobile device, a first encrypted gadget token over a wireless link to an Information Handling System (IHS). The method further including transmitting, by the IHS, an encrypted system token based on the first decrypted gadget token over the wireless link to the mobile device, transmitting, by the mobile device, a second encrypted gadget token based on the decrypted system token over the wireless link to the IHS, authenticating, by the IHS, the second decrypted gadget token, and unlocking the IHS based on the second authenticated gadget token.

14 Claims, 5 Drawing Sheets

302 Initiate Initial Pairing by Creating a First Encrypted Gadget Token and Transmit to IHS

304 Decrypt the First Encrypted Gadget Token and Create an Encrypted System Token

306 Conclude Initial Pairing by Transmitting Encrypted System Token to Gadget

308 Transmit a Second Encrypted Gadget Token When the IHS is In Range

310 IHS Verifies Transmission, Decrypts the Second Encrypted Gadget Token, Autheticates Gadget Token, and Unlocks IHS

KEYLESS ACCESS TO LAPTOP

FIELD OF THE DISCLOSURE

This disclosure generally relates to information handling systems, and more particularly relates to access to information handling systems.

BACKGROUND

As the value and use of information continues to increase, individuals and businesses seek additional ways to process and store information. One option is an information handling system. An information handling system generally processes, compiles, stores, and/or communicates information or data for business, personal, or other purposes. Because technology and information handling needs and requirements may vary between different applications, information handling systems may also vary regarding what information is handled, how the information is handled, how much information is processed, stored, or communicated, and how quickly and efficiently the information may be processed, stored, or communicated. The variations in information handling systems allow for information handling systems to be general or configured for a specific user or specific use such as financial transaction processing, reservations, enterprise data storage, or global communications. In addition, information handling systems may include a variety of hardware and software resources that may be configured to process, store, and communicate information and may include one or more computer systems, data storage systems, and networking systems.

An information handling system (IHS) can be a personal computer, a laptop, a tablet, a server, a smart phone, a smart watch, a smart ring, a smart band, and smart glasses. A user can have multiple IHSs and accounts at multiple network sites, e.g., a social media site, a professional networking site, a banking site, and a shopping site, that can each require user login credentials, e.g., a user identification (userid) and a password, to access and utilize each IHS and account, where the user login credentials may be unique for each IHS and account. With so many IHSs and accounts, it becomes time consuming and challenging for a user to login to each of the user's IHSs and accounts and remember the login credentials of each one.

SUMMARY from the abstract: A method including transmitting, by a mobile device, a first encrypted gadget token over a wireless link to an Information Handling System (IHS). The method further including transmitting, by the IHS, an encrypted system token based on the first decrypted gadget token over the wireless link to the mobile device, transmitting, by the mobile device, a second encrypted gadget token based on the decrypted system token over the wireless link to the IHS, authenticating, by the IHS, the second decrypted gadget token, and unlocking the IHS based on the second authenticated gadget token.

BRIEF DESCRIPTION OF THE DRAWINGS

It will be appreciated that for simplicity and clarity of illustration, elements illustrated in the Figures have not necessarily been drawn to scale. For example, the dimensions of some of the elements are exaggerated relative to other elements. Embodiments incorporating teachings of the present disclosure are shown and described with respect to the drawings presented herein, in which.

The use of the same reference symbols in different drawings indicates similar or identical items.

DETAILED DESCRIPTION OF DRAWINGS

The following description in combination with the Figures is provided to assist in understanding the teachings disclosed herein. The following discussion will focus on specific implementations and embodiments of the teachings. This focus is provided to assist in describing the teachings, and should not be interpreted as a limitation on the scope or applicability of the teachings. However, other teachings can certainly be used in this application. The teachings can also be used in other applications, and with several different types of architectures, such as distributed computing architectures, client/server architectures, or middleware server architectures and associated resources.

For purpose of this disclosure an information handling system can include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, entertainment, or other purposes. For example, an information handling system can be a personal computer, a laptop computer, a smart phone, a tablet device or other consumer electronic device, a network server, a network storage device, a switch router or other network communication device, or any other suitable device and may vary in size, shape, performance, functionality, and price. Further, an information handling system can include processing resources for executing machine-executable code, such as a central processing unit (CPU), a programmable logic array (PLA), an embedded device such as a System-on-a-Chip (SoC), or other control logic hardware. An information handling system can also include one or more computer-readable medium for storing machine-executable code, such as software or data. Additional components of an information handling system can include one or more storage devices that can store machine-executable code, one or more communications ports for communicating with external devices, and various input and output (I/O) devices, such as a keyboard, a mouse, and a video display. An information handling system can also include one or more buses operable to transmit information between the various hardware components.

Figure 1:
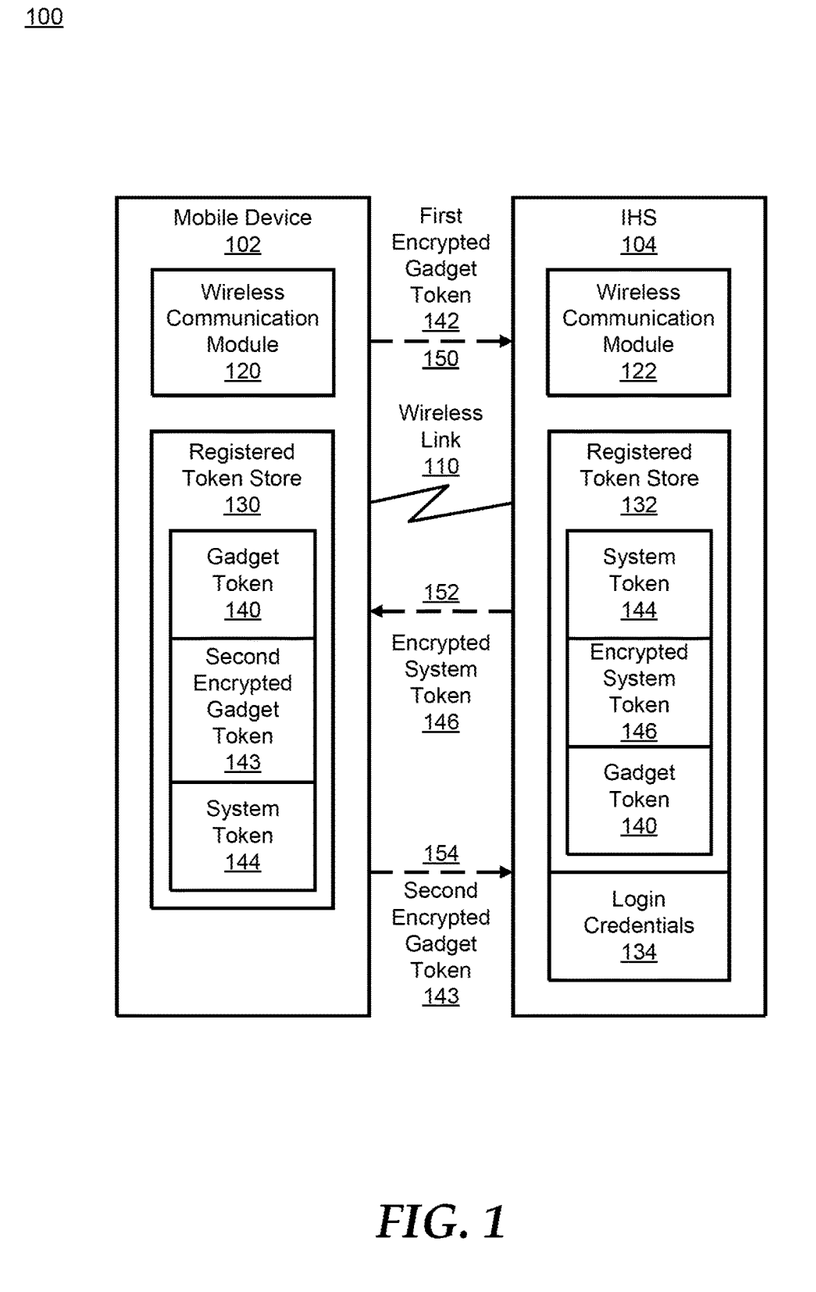
FIG. 1 illustrates a wireless system that provides keyless access to an information handling system according to an embodiment of the present disclosure.

FIG. 1 illustrates a wireless system 100 that provides keyless access to an information handling system including a mobile device 102, also referred herein as a gadget, having a wireless communication module 120 and an information handling system (IHS) 104 having a wireless communication module 122. Mobile device 102 and IHS 104 communicate with each other over a wireless communication link 110. An example of mobile device 102 includes a smart phone, a smart watch, a smart ring, a smart band, smart glasses, and the like. An example of IHS 104 includes a personal computer, a laptop, a tablet, a server, and the like. An example of wireless communication modules 120 and 122 includes a Wireless Local Area Network (WLAN) device, a Bluetooth communication device, a Bluetooth Low Energy (BLE) device, a Near Field Communication (NFC) device, and the like. An example of wireless communication link 110 includes a Wi-Fi link, a Bluetooth link, a Bluetooth Low Energy (BLE) link, a Near Field Communication (NFC) link, and the like.

Mobile device 102 is operable to perform keyless access of IHS 104 using a security method and access information including a security type, user login credentials, (e.g., user identification and password), an identification associated with IHS 104, and an identification associated with mobile device 102, as described in further detail below. The user login credentials and the identification associated with IHS 104 are maintained on IHS 104. In another embodiment, the user login credentials and the identification associated with IHS 104 can be maintained on mobile device 102.

The types of security can include a low level of security and a high level of security. When the low level of security is active, IHS 104 can be unlocked using the user login credentials and the identification associated with IHS 104. When the high level of security is active, IHS 104 can be unlocked using the user login credentials, the identification associated with IHS 104, and the identification associated with the mobile device. Additional security levels and information required to unlock IHS 104 can be defined as needed or desired. The security settings, the user login credentials, and the identifications associated with mobile device 102 and IHS 104 can be configured during a configuration process, a set up process, an update process, and the like. When the login credentials change, e.g., a password is reset, the new password and associated information can be communicated between mobile device 102 and IHS 104 using encryption and public and private keys, and the login credentials can be updated.

During operation mobile device 102 initiates initial pairing with IHS 104 by creating a gadget token 140 and a first encrypted gadget token 142 based on gadget token 140 that are each associated with mobile device 102. Mobile device 102 stores gadget token 140 and associated information at a registered token store 130. Wireless communication module 120 of mobile device 102 then transmits 150 first encrypted gadget token 142 over wireless link 110 to IHS 104, as indicated by the dotted line arrow from mobile device 102 to IHS 104.

Upon receiving first encrypted gadget token 142, IHS 104 decrypts first encrypted gadget token 142 to obtain gadget token 140, associates gadget token 140 with mobile device 102, and creates a system token 144 and an encrypted system token 146 that associates IHS 104 with mobile device 102 based on gadget token 140. IHS 104 stores gadget token 140, system token 144, encrypted system token 146, and associated information at a registered token store 132. Wireless communication module 122 of IHS 104 then transmits 152 encrypted system token 146 over wireless link 110 to mobile device 102, as indicated by the dotted line arrow from IHS 104 to mobile device 102.

Upon receiving encrypted system token 146, mobile device 102, decrypts encrypted system token 146 to obtain system token 144, associates system token 144 with gadget token 140, creates a second encrypted gadget token 143 based on gadget token 140 and system token 144, and updates registered token store 130 with second encrypted gadget token 143, system token 144 and associated information. At this point, the initial pairing of mobile device 102 and IHS 104 is concluded. When mobile device 102 detects that IHS 104 is in range, wireless communication module 120 of mobile device 102 transmits 154 second encrypted gadget token 143 over wireless link 110 to IHS 104, as indicated by the dotted line arrow from mobile device 102 to IHS 104.

Upon receiving encrypted gadget token 142, IHS 104 verifies the transmission of second encrypted gadget token 143 is from mobile device 102, decrypts second encrypted gadget token 143 to obtain gadget token 140, authenticates gadget token 140 based on information at registered token store 132 by determining that gadget token 140 is the same as gadget token 140 stored at registered token store 132, and unlocks IHS 104 based on authenticated gadget token 140, login credentials 134, and the identification associated with IHS 104, where the low level of security is active for the security method, as previously described. In another embodiment, IHS 104 is unlocked based on authenticated gadget token 140, login credentials 134, the identification associated with IHS 104, and the identification associated with mobile device 102, where the high level of security is active for the security method, as previously described. By mobile device 102 maintaining both gadget token 140 and second encrypted gadget token 143 at registered token store 130, and IHS 104 maintaining both system token 144 and encrypted system token 146 at registered token store 132, performance can be improved by not requiring an encryption algorithm to be run on all subsequent communications between mobile device 102 and IHS 104 after the initial pairing process has been completed.

Figure 2:
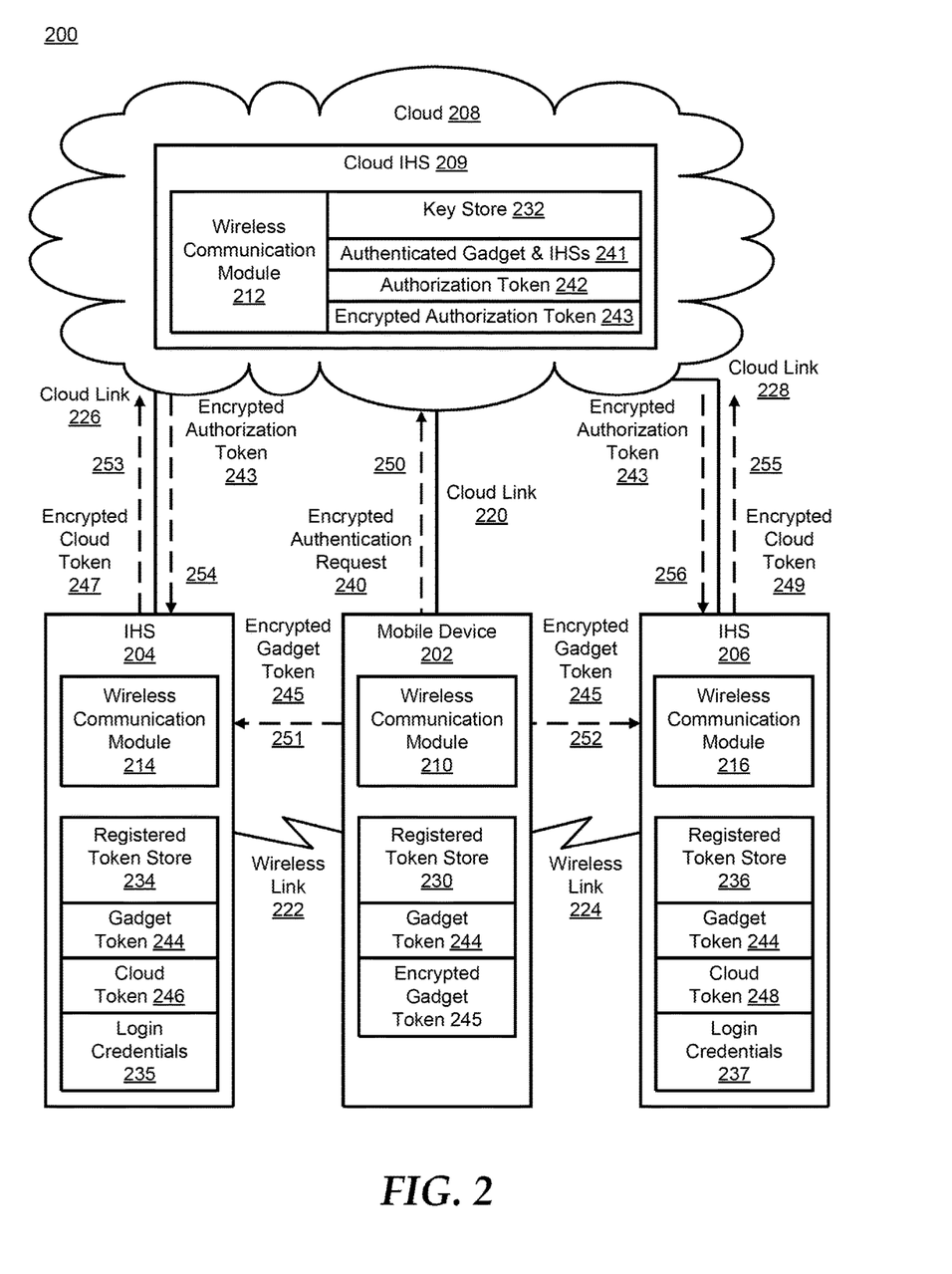
FIG. 2 illustrates another wireless system that provides keyless access to more than one information handling system according to an embodiment of the present disclosure.

FIG. 2 illustrates another wireless system 200 that provides keyless access to more than one information handling system (IHS) including a mobile device 202 having a wireless communication module 210 and a registered token store 230, an IHS 204 having a wireless communication module 214 and a registered token store 234, an IHS 206 having a wireless communication module 216 and a registered token store 236, and a cloud 208 having a cloud IHS 209 that includes a wireless communication module 212 and a key store 232. Mobile device 202, and IHSs 204 and 206 communicate with each other over wireless communication links 222 and 224, respectively, and with cloud IHS 209 over cloud links 220, 226, and 228, respectively. Mobile device 202 is similar in functionality and structure of mobile device 102. IHSs 204, 206, and 209 are similar in functionality and structure of IHS 104. Wireless communication links 222 and 224 are similar in functionality and structure of wireless communication link 110. An example of cloud links 220, 226, and 228 includes a network link, an internet link, a Wi-Fi link, a Bluetooth link, a Bluetooth Low Energy (BLE) link, and a Near Field Communication (NFC) link, and the like.

Wireless communication system 200 is operable to perform keyless access of IHSs 204 and 206 using the security method and the access information, previously described, including the security type, the user login credentials, identifications associated with IHSs 204 and 206, respectively, and an identification associated with mobile device 202, as described in further detail below.

Key store 232 can be initialized during a configuration process, an initialization process, an update process, a management process, and the like, prior to any keyless access processing. This allows IHS 209 of cloud 208 to create and maintain a list of authenticated gadgets and IHSs 241, associated authorization tokens 242, and associated encrypted authorization tokens 243 at key store 232 that each indicate which gadget is authenticated to unlock IHSs 241 associated with that gadget. Authorization token 242 is for all IHSs that mobile device 202 is authorized to unlock. Authorization token 242 can also be configured to have multiple tokens which are associated with registered IHSs included in IHSs 241. Key store 232 can include one or more authenticated gadget and IHSs and their associated authorization token and encrypted authorization token entries that are maintained by IHS 209.

During operation, mobile device 202 performs an identification process to determine which IHSs it is authorized to unlock. Mobile device 202 then creates an authentication request for a combination of mobile device 202 and IHSs 204 and 206, creates an encrypted authentication request 240, and transmits 250 encrypted authentication request 240 over cloud link 220 to cloud IHS 209, as indicated by the dotted line arrow from mobile device 202 to IHS 209. Upon receiving encrypted authentication request 240, cloud IHS 209 decrypts encrypted authentication request 240 to obtain an authentication request, authenticates that mobile device 202 is authorized to unlock IHSs 204 and 206 based on the authentication request, and the information at a key store 232 associated with mobile device 202, where cloud IHS 209 determines that mobile device 202 is authorized to unlock IHSs 204 and 206 by matching the authentication request with an entry of the list of authenticated gadgets and IHSs 241 stored at key store 232.

Mobile device 202 creates a gadget token 244 and an encrypted gadget token 245, stores gadget token 244 and encrypted gadget token 245 at registered token store 230. Wireless communication module 210 of mobile device 202 transmits 251 encrypted gadget token 245 over wireless link 222 to IHS 204 when IHS 204 is in range, as indicated by the dotted line arrow from mobile device 202 to IHS 204. Wireless communication module 210 of mobile device 202 also transmits 252 encrypted gadget token 245 over wireless link 224 to IHS 206 when IHS 206 is in range, as indicated by the dotted line arrow from mobile device 202 to IHS 206.

Upon receiving encrypted gadget token 245, IHS 204 decrypts encrypted gadget token 245 to obtain gadget token 244, creates a cloud token 246 based on gadget token 244, creates encrypted cloud token 247, and stores gadget token 244 and cloud token 246 at registered token store 234. Wireless communication module 214 transmits 253 encrypted cloud token 247 over cloud link 226 to cloud IHS 209, as indicated by the dotted line arrow from IHS 204 to IHS 209. Upon receiving encrypted gadget token 245, IHS 206 decrypts encrypted gadget token 245 to obtain gadget token 244, creates a cloud token 248 based on gadget token 244, creates an encrypted cloud token 249, and stores gadget token 244 and cloud token 248 at registered token store 236. Wireless communication module 216 transmits 255 encrypted cloud token 249 over cloud link 228 to cloud IHS 209, as indicated by the dotted line arrow from IHS 206 to IHS 209.

Upon receiving encrypted cloud token 247 from IHS 204, IHS 209 decrypts encrypted cloud token 247 to obtain cloud token 246 and authenticates cloud token 246 based on information at key store 232 associated with cloud token 246 and the identification associated with IHS 204, where the low level of security is active for the security method, as previously described. In another embodiment, IHS 209 authenticates cloud token 246 based on information at key store 232 associated with cloud token 246, the identification associated with IHS 204, and the identification associated with mobile device 202, where the high level of security is active for the security method, as previously described. IHS 209 authenticates cloud token 246 by matching information of cloud token 246 with information of the list of authenticated gadgets and IHSs 241. Once cloud token 246 has been authenticated, IHS 209 releases authorization token 242. Wireless communication module 212 transmits 254 encrypted authorization token 243 associated with cloud token 246 over cloud link 226 to IHS 204, as indicated by the dotted line arrow from IHS 209 to IHS 204.

Upon receiving encrypted cloud token 249 from IHS 206, IHS 209 decrypts encrypted cloud token 249 to obtain cloud token 248 and authenticates cloud token 248 based on information at key store 232 associated with cloud token 248 and the identification associated with IHS 206, where the low level of security is active for the security method, as previously described. In another embodiment, IHS 209 authenticates cloud token 248 based on information at key store 232 associated with cloud token 248, the identification associated with IHS 206, and the identification associated with mobile device 202, where the high level of security is active for the security method, as previously described. IHS 209 authenticates cloud token 248 by matching information of cloud token 248 with information of the list of authenticated gadgets and IHSs 241. Once cloud token 248 has been authenticated, IHS 209 releases authorization token 242. Wireless communication module 212 transmits 256 encrypted authorization token 243 associated with cloud token 248 over cloud link 228 to IHS 206, as indicated by the dotted line arrow from IHS 209 to IHS 206.

Upon receiving encrypted authorization token 243 from IHS 209, IHS 204 verifies the transmission 254 of encrypted authorization token 243 is from IHS 209, decrypts encrypted authorization token 243 to obtain authorization token 242, and verifies authorization token 242 based on information at registered token store 234, where IHS 204 verifies authorization token 242 by matching information of authorization token 242 with information of cloud token 246. IHS 204 then authorizes authorization token 242 and unlocks IHS 204 based on authorization token 242, login credentials 235, and the identification associated with IHS 204. In another embodiment, IHS 204 is unlocked based on authorization token 242, login credentials 235, the identification associated with IHS 204, and the identification associated with mobile device 202.

Upon receiving encrypted authorization token 243 from IHS 209, IHS 206 verifies the transmission 256 of encrypted authorization token 243 is from IHS 209, decrypts encrypted authorization token 243 to obtain authorization token 242, and verifies authorization token 242 based on information at registered token store 236, where IHS 206 verifies authorization token 242 by matching information of authorization token 242 with information of cloud token 248. IHS 206 then authorizes authorization token 242 and unlocks IHS 206 based on authorization token 242, login credentials 237, and the identification associated with IHS 206. In another embodiment, IHS 206 is unlocked based on authorization token 242, login credentials 237, the identification associated with IHS 206, and the identification associated with mobile device 202.

In this manner, a user can login to each of the user's IHSs and accounts at multiple networking sites by bring the user's mobile device in range of the user's IHSs without the need to remember the login credentials of each one. This also reduces the complexity and time required to login to each one.

Figure 3:
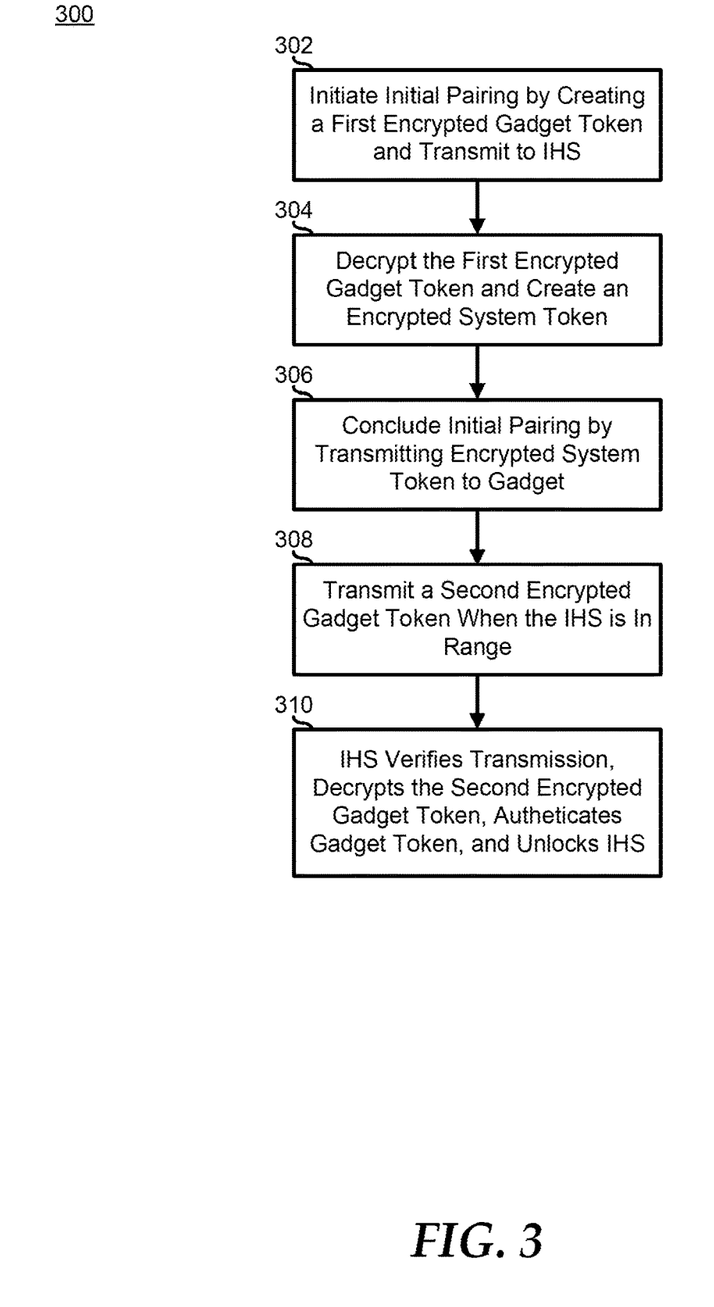
FIG. 3 a method of providing keyless access to an information handling system according to an embodiment of the present disclosure.

FIG. 3 illustrates a method 300 of providing keyless access to an information handling system (IHS), where the exemplary method 300 starts at block 302. At block 302, a mobile device initiates initial pairing with the IHS by creating and encrypting a gadget token associated with the mobile device to obtain a first encrypted gadget token. The mobile device stores the gadget token and associated information at a registered token store of the mobile device. A wireless communication module of the mobile device then transmits the first encrypted gadget token over a wireless link to the IHS.

At block 304, upon receiving the first encrypted gadget token, the IHS decrypts the encrypted gadget token to obtain the gadget token, associates the gadget token with the mobile device based on the gadget token, and creates and encrypts a system token associated with the mobile device based on the gadget token. The IHS stores the gadget token, the system token, the encrypted system token, and associated information at a registered token store of the IHS. At block 306, the IHS concludes the initial pairing by transmitting, by a wireless communication module of the IHS, the encrypted system token over the wireless link to the mobile device.

At block 308, upon receiving the encrypted system token, the mobile device decrypts the encrypted system token to obtain the system token, associates the system token with the gadget token, creates a second encrypted gadget token based on the gadget token and the system token, and updates the registered token store with the second encrypted gadget token, the system token and associated information. At this point, the initial pairing of the mobile device and the IHS has concluded. When the mobile device detects that the IHS is in range, the wireless communication module transmits the second encrypted gadget token over the wireless link to the IHS.

At block 310, upon receiving the second encrypted gadget token, the IHS verifies the transmission of the second encrypted gadget token is from the mobile device, decrypts the second encrypted gadget token to obtain the gadget token, authenticates the gadget token based on information at the registered token store, and unlocks the IHS based on the authenticated gadget token, the login credentials of the IHS, and the identification associated with the IHS. At this point, method 300 of providing keyless access to an IHS, the IHS, has completed.

Figure 4:
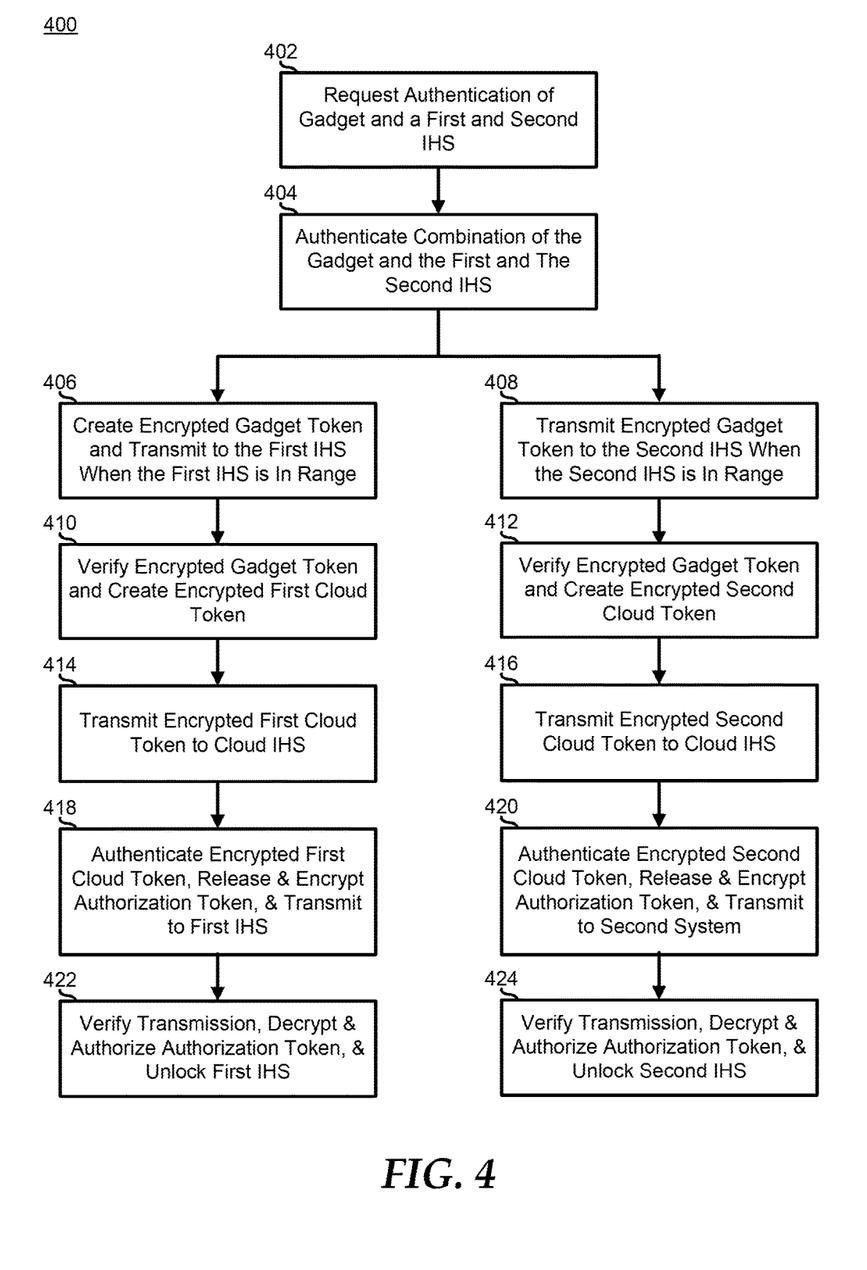
FIG. 4 a method of providing keyless access to more than one information handling system according to an embodiment of the present disclosure.

FIG. 4 a method 400 of providing keyless access to more than one information handling system, where the exemplary method 400 starts at block 402. At block 402, a mobile device creates an authentication request for a combination of the mobile device, a first IHS and a second IHS, creates an encrypted authentication request, and transmits the encrypted authentication request over a cloud link to a cloud IHS. At block 404, upon receiving the encrypted authentication request, the cloud IHS decrypts the encrypted authentication request to obtain the authentication request, authenticates that the mobile device is authorized to unlock the first and second IHSs based on the authentication request, and the information at a key store associated with the mobile device, where the cloud IHS determines that the mobile device is authorized to unlock the first and second IHSs by matching the authentication request with an authenticated gadget and IHSs stored at the key store. At block 406, the mobile device creates a gadget token and an encrypted gadget token, stores the gadget token and the encrypted gadget token at a registered token store. A wireless communication module of the mobile device transmits the encrypted gadget token over a first wireless link to the first IHS when the first IHS is in range. At block 408, the wireless communication module transmits the encrypted gadget token over a second wireless link to the second IHS when the second IHS is in range.

At block 410, upon receiving the encrypted gadget token, the first IHS decrypts the encrypted gadget token to obtain the gadget token, creates a cloud token based on the gadget token, creates an encrypted cloud token, and stores the gadget token and the cloud token at a registered token store. At block 412, upon receiving the encrypted gadget token, the second IHS decrypts the encrypted gadget token to obtain the gadget token, creates a cloud token based on the gadget token, creates an encrypted cloud token, and stores the gadget token and the cloud token at a registered token store. At block 414, a wireless communication module transmits the encrypted cloud token over a cloud link to the cloud IHS. At block 416, a wireless communication module transmits the encrypted cloud token over a cloud link to the cloud IHS.

At block 418, upon receiving the encrypted cloud token from the first IHS, the cloud IHS decrypts the encrypted cloud token to obtain the cloud token and authenticates the cloud token based on information at the key store associated with the cloud token and the identification associated with the first IHS, where the low level of security is active for the security method. In another embodiment, the cloud IHS authenticates the cloud token based on information at the key store associated with the cloud token, the identification associated with the first IHS, and the identification associated with the mobile device, where the high level of security is active for the security method. The cloud IHS authenticates the cloud token by matching information of the cloud token with information of the authenticated gadget and the first and second IHSs. Once the cloud token has been authenticated, the cloud IHS releases the authorization token. A wireless communication module transmits an encrypted authorization token associated with the cloud token over the cloud link to the first IHS.

At block 420, upon receiving the encrypted cloud token from the second IHS, the cloud IHS decrypts the encrypted cloud token to obtain the cloud token and authenticates the cloud token based on information at the key store associated with the cloud token and the identification associated with the second IHS, where the low level of security is active for the security method. In another embodiment, the cloud IHS authenticates the cloud token based on information at the key store associated with the cloud token, the identification associated with the second IHS, and the identification associated with the mobile device, where the high level of security is active for the security method. The cloud IHS authenticates the cloud token by matching information of the cloud token with information of the authenticated gadget and the first and second IHSs. Once the cloud token has been authenticated, the cloud IHS releases the authorization token. A wireless communication module transmits an encrypted authorization token associated with the cloud token over the cloud link to the second IHS.

At block 422, upon receiving the encrypted authorization token from the cloud IHS, the first IHS verifies the transmission of the encrypted authorization token is from the cloud IHS, decrypts the encrypted authorization token to obtain the authorization token, and verifies the authorization token based on information at the registered token store, where the first IHS verifies the authorization token by matching information of the authorization token with information of the cloud token. The first IHS then authorizes the authorization token and unlocks the first IHS based on the authorization token, login credentials, and the identification associated with the first IHS. In another embodiment, the first IHS is unlocked based on the authorization token, the login credentials, the identification associated with the first IHS, and the identification associated with the mobile device.

At block 424, upon receiving the encrypted authorization token from the cloud IHS, the second IHS verifies the transmission of the encrypted authorization token is from the cloud IHS, decrypts the encrypted authorization token to obtain the authorization token, and verifies the authorization token based on information at the registered token store, where the second IHS verifies the authorization token by matching information of the authorization token with information of the cloud token. The second IHS then authorizes the authorization token and unlocks the second IHS based on the authorization token, login credentials, and the identification associated with the second IHS. In another embodiment, the second IHS is unlocked based on the authorization token, the login credentials, the identification associated with the second IHS, and the identification associated with the mobile device. At this point, method 400 of providing keyless access to more than one IHS, the first and second IHSs, has completed.

Figure 5:
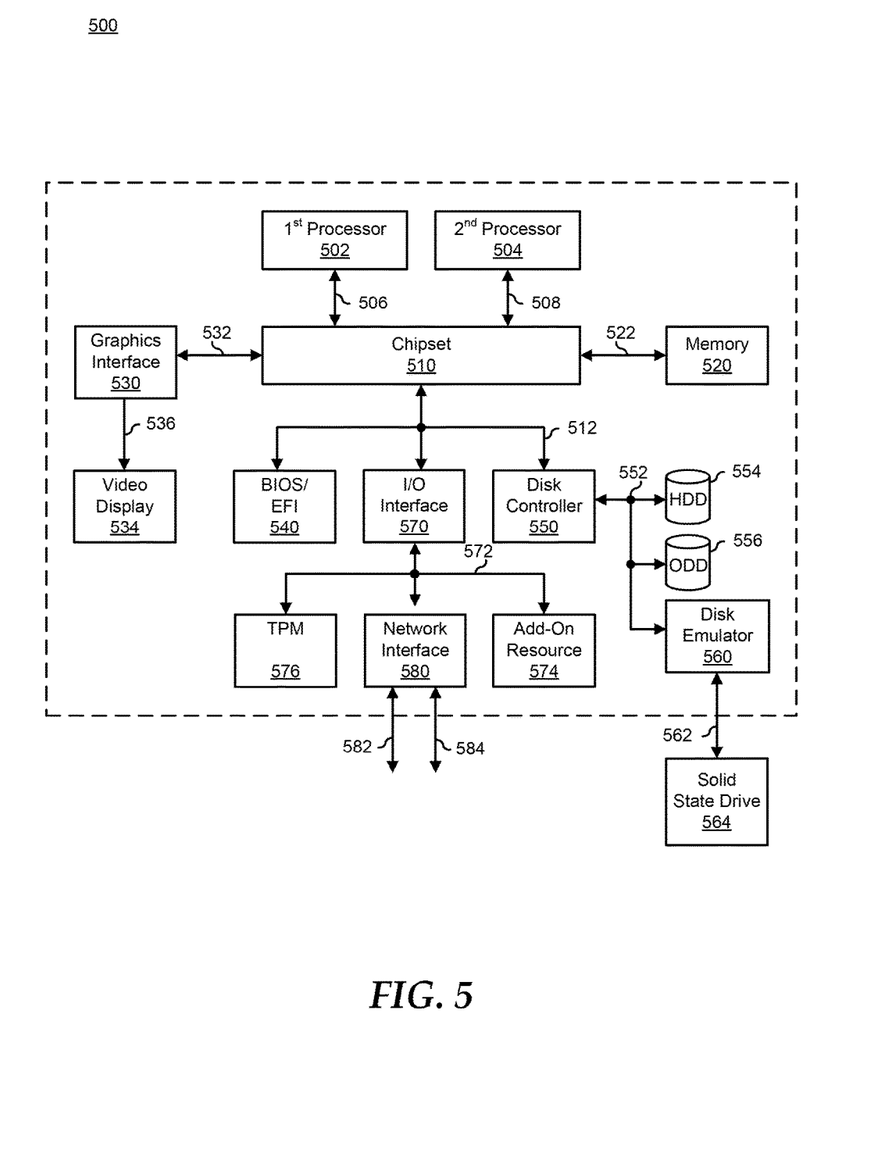
FIG. 5 is a block diagram illustrating a generalized information handling system according to an embodiment of the present disclosure.

FIG. 5 illustrates a generalized embodiment of information handling system 500. For purpose of this disclosure information handling system 500 can include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, entertainment, or other purposes. For example, information handling system 500 can be a personal computer, a laptop computer, a smart phone, a tablet device or other consumer electronic device, a network server, a network storage device, a switch router or other network communication device, or any other suitable device and may vary in size, shape, performance, functionality, and price. Further, information handling system 500 can include processing resources for executing machine-executable code, such as a central processing unit (CPU), a programmable logic array (PLA), an embedded device such as a System-on-a-Chip (SoC), or other control logic hardware. Information handling system 500 can also include one or more computer-readable medium for storing machine-executable code, such as software or data. Additional components of information handling system 500 can include one or more storage devices that can store machine-executable code, one or more communications ports for communicating with external devices, and various input and output (I/O) devices, such as a keyboard, a mouse, and a video display. Information handling system 500 can also include one or more buses operable to transmit information between the various hardware components.

Information handling system 500 can include devices or modules that embody one or more of the devices or modules described above, and operates to perform one or more of the methods described above. Information handling system 500 includes a processors 502 and 504, a chipset 510, a memory 520, a graphics interface 530, include a basic input and output system/extensible firmware interface (BIOS/EFI) module 540, a disk controller 550, a disk emulator 560, an input/output (I/O) interface 570, and a network interface 580. Processor 502 is connected to chipset 510 via processor interface 506, and processor 504 is connected to the chipset via processor interface 508. Memory 520 is connected to chipset 510 via a memory bus 522. Graphics interface 530 is connected to chipset 510 via a graphics interface 532, and provides a video display output 536 to a video display 534. In a particular embodiment, information handling system 500 includes separate memories that are dedicated to each of processors 502 and 504 via separate memory interfaces. An example of memory 520 includes random access memory (RAM) such as static RAM (SRAM), dynamic RAM (DRAM), non-volatile RAM (NV-RAM), or the like, read only memory (ROM), another type of memory, or a combination thereof.

BIOS/EFI module 540, disk controller 550, and I/O interface 570 are connected to chipset 510 via an I/O channel 512. An example of I/O channel 512 includes a Peripheral Component Interconnect (PCI) interface, a PCI-Extended (PCI-X) interface, a high-speed PCI-Express (PCIe) interface, another industry standard or proprietary communication interface, or a combination thereof. Chipset 510 can also include one or more other I/O interfaces, including an Industry Standard Architecture (ISA) interface, a Small Computer Serial Interface (SCSI) interface, an Inter-Integrated Circuit ($I^2C$) interface, a System Packet Interface (SPI), a Universal Serial Bus (USB), another interface, or a combination thereof. BIOS/EFI module 540 includes BIOS/EFI code operable to detect resources within information handling system 500, to provide drivers for the resources, initialize the resources, and access the resources. BIOS/EFI module 540 includes code that operates to detect resources within information handling system 500, to provide drivers for the resources, to initialize the resources, and to access the resources.

Disk controller 550 includes a disk interface 552 that connects the disc controller to a hard disk drive (HDD) 554, to an optical disk drive (ODD) 556, and to disk emulator 560. An example of disk interface 552 includes an Integrated Drive Electronics (IDE) interface, an Advanced Technology Attachment (ATA) such as a parallel ATA (PATA) interface or a serial ATA (SATA) interface, a SCSI interface, a USB interface, a proprietary interface, or a combination thereof. Disk emulator 560 permits a solid-state drive 564 to be connected to information handling system 500 via an external interface 562. An example of external interface 562 includes a USB interface, an IEEE 1394 (Firewire) interface, a proprietary interface, or a combination thereof. Alternatively, solid-state drive 564 can be disposed within information handling system 500.

I/O interface 570 includes a peripheral interface 572 that connects the I/O interface to an add-on resource 574, to a TPM 576, and to network interface 580. Peripheral interface 572 can be the same type of interface as I/O channel 512, or can be a different type of interface. As such, I/O interface 570 extends the capacity of I/O channel 512 when peripheral interface 572 and the I/O channel are of the same type, and the I/O interface translates information from a format suitable to the I/O channel to a format suitable to the peripheral channel 572 when they are of a different type. Add-on resource 574 can include a data storage system, an additional graphics interface, a network interface card (NIC), a sound/video processing card, another add-on resource, or a combination thereof. Add-on resource 574 can be on a main circuit board, on separate circuit board or add-in card disposed within information handling system 500, a device that is external to the information handling system, or a combination thereof.

Network interface 580 represents a NIC disposed within information handling system 500, on a main circuit board of the information handling system, integrated onto another component such as chipset 510, in another suitable location, or a combination thereof. Network interface device 580 includes network channels 582 and 584 that provide interfaces to devices that are external to information handling system 500. In a particular embodiment, network channels 582 and 584 are of a different type than peripheral channel 572 and network interface 580 translates information from a format suitable to the peripheral channel to a format suitable to external devices. An example of network channels 582 and 584 includes InfiniBand channels, Fibre Channel channels, Gigabit Ethernet channels, proprietary channel architectures, or a combination thereof. Network channels 582 and 584 can be connected to external network resources (not illustrated). The network resource can include another information handling system, a data storage system, another network, a grid management system, another suitable resource, or a combination thereof.

Although only a few exemplary embodiments have been described in detail herein, those skilled in the art will readily appreciate that many modifications are possible in the exemplary embodiments without materially departing from the novel teachings and advantages of the embodiments of the present disclosure. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

The above-disclosed subject matter is to be considered illustrative, and not restrictive, and the appended claims are intended to cover any and all such modifications, enhancements, and other embodiments that fall within the scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A method comprising:
transmitting, by a mobile device, an authentication request to a cloud information handling system (IHS) to determine that the mobile device is authorized to unlock a node IHS;
determining, by the mobile device, that the node IHS is within range of a near field communication interface of the mobile device;
transmitting, by the mobile device, an encrypted gadget token over the wireless interface between the mobile device and the node IHS in response to determining that the node IHS is within range;
transmitting, by the node IHS, an encrypted cloud token based on the encrypted gadget token over a communication link between the node IHS and a cloud IHS;
authenticating, by the cloud IHS, the encrypted cloud token;
transmitting, by the cloud IHS, an encrypted authentication token based on the encrypted cloud token over the communication link to the node IHS;
verifying, by the node IHS, that the transmission of the encrypted gadget token is from the mobile device;
authenticating, by the node IHS, the encrypted authentication token; and
unlocking the node IHS based on the authenticating of the encrypted authentication token.

2. The method of claim 1, further comprising:
creating a gadget token prior to transmitting the encrypted gadget token.

3. The method of claim 2, further comprising:
decrypting, by the node IHS, the encrypted gadget token to obtain the gadget token; and
creating a cloud token based on the gadget token prior to transmitting the encrypted cloud token.

4. The method of claim 2, further comprising:
storing, by the mobile device, the gadget token at a registered token store of the mobile device.

5. The method of claim 1, wherein the wireless link comprises one of a WI-FI link, a Bluetooth link, a Bluetooth Low Energy (BLE) link, and a Near Field Communication (NFC) link.

6. A wireless authentication system comprising:
a mobile device having a first wireless communication module; and
a node Information Handling System (IHS) having a second wireless communication module to provide a wireless link to the mobile device via the first wireless communication module;
wherein the mobile device is configured to:
transmit an authentication request to a cloud IHS to determine that the mobile device is authorized to unlock the node IHS;
determine that the node IHS is within range of a near field communication interface of the mobile device; and
transmit an encrypted gadget token over the wireless link to the IHS in response to determining that the node IHS is within range;
wherein the node IHS is configured to transmit an encrypted cloud token based on the encrypted gadget token over a communication link to an authentication system, to receive an encrypted authentication token over the communication link from the authentication system, to verify that the transmission of the encrypted gadget token is from the mobile device, and to unlock the node IHS based on the encrypted authentication token, wherein the encrypted authentication token is based on the encrypted cloud token.

7. The wireless authentication system of claim 6, the mobile device further configured to create a gadget token prior to the transmission of the encrypted gadget token.

8. The wireless authentication system of claim 7, the node IHS further configured to:
decrypt the encrypted gadget token to obtain the gadget token; and
create the encrypted cloud token based on the gadget token prior to transmitting the encrypted cloud token.

9. The wireless authentication system of claim 7, the mobile device further configured to store the gadget token at a registered token store of the mobile device.

10. The wireless authentication system of claim 6, wherein the wireless link comprises one of a Wi-Fi link, a Bluetooth link, a Bluetooth Low Energy (BLE) link, and a Near Field Communication (NFC) link.

11. A wireless authentication system comprising:
a mobile device;
a first information handling system coupled to the mobile device via a first wireless link;
a second information handling system coupled to the mobile device via a second wireless link; and
an authentication system;

wherein the mobile device is configured to:
  transmit an authentication request to a cloud IHS to determine that the mobile device is authorized to unlock the first and second information handling systems;
  determine that the first information handling system is within range of a near field communication interface of the mobile device;
  transmit a first encrypted gadget token over the first wireless link to the first information handling system in response to determining that the first information handling system is within range; and
  transmit a second encrypted gadget token over the second wireless link to the second information handling system;
wherein the first information handling system is configured to transmit a first encrypted cloud token based on the first encrypted gadget token over a first communication link to the authentication system;
wherein the second information handling system is configured to transmit a second encrypted cloud token based on the second encrypted gadget token over a second communication link to the authentication system;
wherein the authentication system is configured to:
  authenticate the first and second encrypted cloud tokens;
  transmit a first encrypted authentication token based on the first encrypted cloud token over the first communication link to the first information handling system; and
  transmit a second encrypted authentication token based on the second encrypted cloud token over the second communication link to the second information handling system;
wherein the first information handling system is further configured to verify that the transmission of the first encrypted gadget token is from the mobile device, and to unlock the first information handling system based on the first encrypted authentication token; and
wherein the second information handling system is further configured to unlock the second information handling system based on the second encrypted authentication token.

12. The wireless authentication system of claim 11, the mobile device further configured to:
  create a gadget token prior to the transmission of the first encrypted gadget token.

13. The wireless authentication system of claim 12, the first information handling system further configured to:
  decrypt the first encrypted gadget token to obtain the gadget token; and
  create the first encrypted cloud token based on the gadget token prior to transmitting the first encrypted cloud token.

14. The wireless authentication system of claim 12, the mobile device further configured to:
  store the gadget token at a registered token store of the mobile device.

* * * * *